United States Patent
Minamitani et al.

(10) Patent No.: US 9,804,077 B2
(45) Date of Patent: Oct. 31, 2017

(54) DEVICE AND METHOD FOR MONITORING CORROSIVE ENVIRONMENT

(71) Applicant: Hitachi, Ltd., Chiyoda-ku, Tokyo (JP)

(72) Inventors: Rintarou Minamitani, Tokyo (JP); Noriyuki Kushida, Tokyo (JP); Tetsuya Ideno, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 226 days.

(21) Appl. No.: 14/712,025

(22) Filed: May 14, 2015

(65) Prior Publication Data

US 2015/0330889 A1 Nov. 19, 2015

(30) Foreign Application Priority Data

May 16, 2014 (JP) .................. 2014-101902

(51) Int. Cl.
*G01N 17/04* (2006.01)
*G01N 27/20* (2006.01)

(52) U.S. Cl.
CPC ............. *G01N 17/04* (2013.01); *G01N 27/20* (2013.01)

(58) Field of Classification Search
CPC ........ G01N 17/02; G01N 17/00; G01N 17/04; G01N 27/041; G01N 27/20
See application file for complete search history.

(56) References Cited

U.S. PATENT DOCUMENTS

| 5,411,890 A * | 5/1995 | Falat ...................... G01N 17/00 422/53 |
| 2002/0078752 A1 | 6/2002 | Braunling et al. |
| 2005/0082174 A1 * | 4/2005 | Kendig .................. G01N 17/02 205/775.5 |
| 2012/0038377 A1 * | 2/2012 | Hamann ................ G01N 27/00 324/700 |
| 2013/0265064 A1 * | 10/2013 | Hamann ................ G01N 17/04 324/700 |

FOREIGN PATENT DOCUMENTS

| CN | 1598551 A | 3/2005 |
| CN | 1605853 A | 4/2005 |
| JP | 2003-294606 A | 10/2003 |

OTHER PUBLICATIONS

Chinese-language Office Action issued in counterpart Chinese Application No. 201510246813.3 dated Jul. 4, 2017 (Nine (9) pages).

* cited by examiner

*Primary Examiner* — Jermele M Hollington
*Assistant Examiner* — Suresh K Rajaputra
(74) *Attorney, Agent, or Firm* — Crowell & Moring LLP

(57) ABSTRACT

Provided is a device for monitoring corrosive environment including at least one passage structure having an opening and configured to control intrusion of a corrosive substance present in an atmosphere; and a sensor unit having a metal film that is disposed inside the passage structure. The metal film inside the passage structure corrodes by the corrosive substance intruding from the opening to the passage structure. During the monitoring, an electric resistance value of the metal film varies depending on expansion of the corroded region of the metal film. Thus, the device for monitoring corrosive environment measures the electric resistance value of the metal film with suppressing fluctuation of the measured values. This allows a corrosion level of the environment installed with electric and electronic apparatuses to be evaluated for a long term and in an accurate manner.

17 Claims, 8 Drawing Sheets

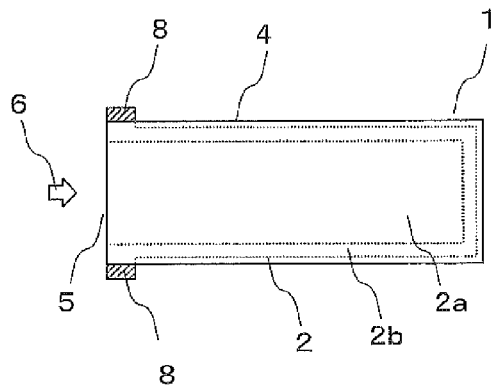
FIG.1
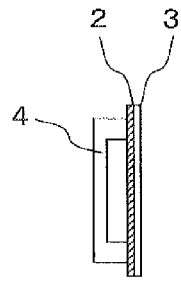
FIG.2
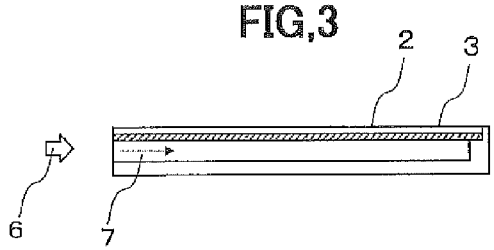
FIG.3
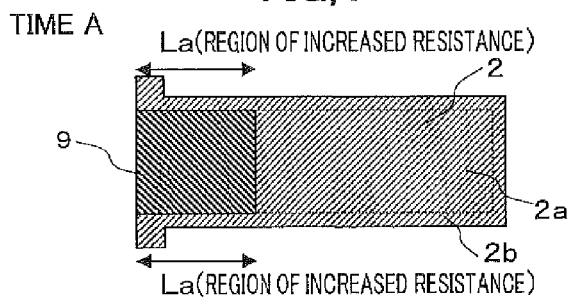
FIG.4 TIME A
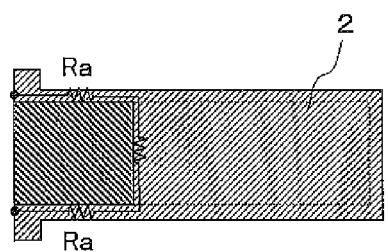
FIG.5
FIG.6
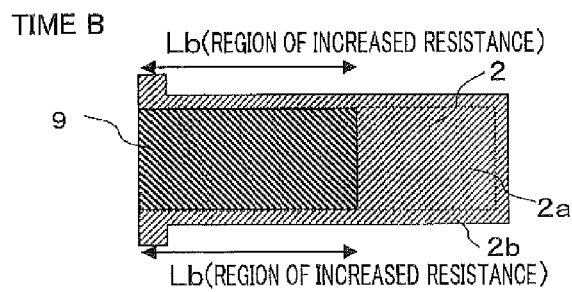
FIG.7 TIME B
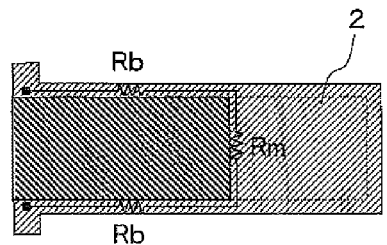
FIG.8
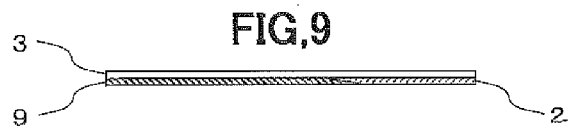
FIG.9

TIME A

TIME B

TIME A

TIME B

TIME A

TIME B

FIG. 42
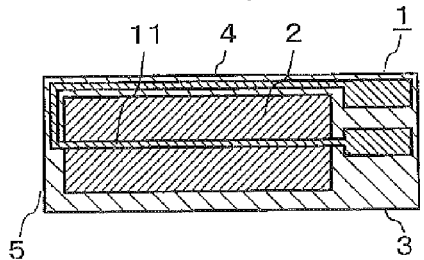
FIG. 43
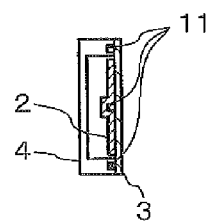
FIG. 44
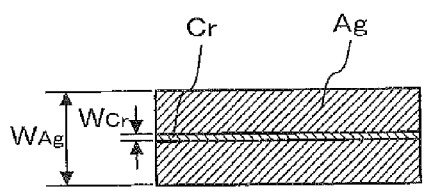
FIG. 45
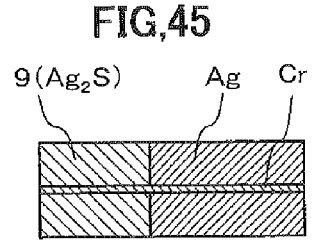
FIG. 46
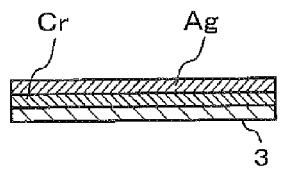
FIG. 47
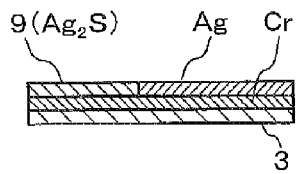
FIG. 48
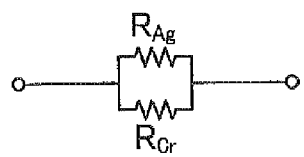
FIG. 49
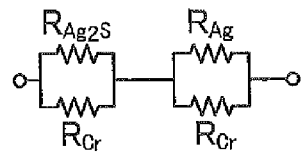
FIG. 50
|  | MEASURED VALUE OF RESISTIVITY ($\Omega$m@20°C) | LITERATURE VALUE OF RESISTIVITY ($\Omega$m@20°C) | MEASURED VALUE OF TCR (1/°C$\Omega$m@20°C) | LITERATURE VALUE OF TCR (1/°C) |
|---|---|---|---|---|
| Ag | 2.84~2.88E-8 | 1.59E-8 | 2.07~2.14E-3 | 6.1E-3 |
| $Ag_2S$ | 4.52E-5 | – | -4.89E-3 |  |
| Cr | 7.38~7.56E-7 | 1.29E-7 | (2.47)~4.49E-5 | 5.9E-5 |
| Ti | 2.58E-6 | 4.27E-7 | 7.36E-4 |  |
| IZO |  | 3E-6 |  |  |

DEVICE AND METHOD FOR MONITORING CORROSIVE ENVIRONMENT

BACKGROUND OF THE INVENTION

1. Field of the Invention

The present invention relates to a device for monitoring corrosive environment and a method for monitoring corrosive environment, both targeting an indoor environment, mainly an environment installed with electric and electronic apparatuses. A level of corrosion generated by a corrosive gas present in the environment is measured by the device and method for monitoring corrosive environment.

2. Related Art

Japanese Unexamined Patent Application Publication No. 2003-294606 (i.e., Patent Document 1) discloses background art of the invention. That is, the environment evaluation apparatus of Patent Document 1 basically includes 1) an element unit for reacting with gas components in an environment, 2) a unit for detecting a change in the element unit and converting the detected change into an electric signal, and 3) a storage unit for storing the detected data. Specifically, the element unit is formed by using a plurality of metal films, for example, a metal film with a thickness of 0.1 μm made of silver, copper, iron, and stainless steel. Herein, evaluating a material in an environment is performed by measuring a time course of at least one property selected from the light reflection, light transparency and electric resistance of the metal film, thereby detecting gas components in the environment.

When the time course of the electric resistance value is measured, a change in the electric resistance value caused by the change in the whole metal film (e.g., entire surface corrosion) may be measured. This measurement allows a thickness of the corroded metal film to be calculated, thereby to easily afford a corrosive rate thereof.

Note that a gas detection system detects a change in an element, and converts the detected change into an electric signal. The gas detection system includes a gas introduction unit and a gas detection element (i.e., corresponding to the sensor unit of the present invention). Those gas components are guided to the gas detection element by a suction pump of the gas introduction unit. As mentioned above, under circumstances as the global environment changes, it is advantageous to provide a measuring apparatus greatly useful for evaluating various materials located in such environment.

Here, long term reliability is required for electric and electronic apparatuses in order to stably operate target equipment. Further, a lot of electric and electronic components, which include a fine wiring structure and a film plating structure both applied with a high density mounting structure, are mounted on the target equipment to achieve high speed operation and space-saving arrangement. In those electric and electronic components, even slightly corroded damage may change the electric property or magnetic property of the components to cause a failure or malfunction. Therefore, suppression of the corroded damage is an important issue to improve the reliability of the electric and electronic apparatuses. Eventually, continuous evaluation in easy, a short period and high accuracy of corrosive environment installed with electric and electronic apparatuses is demanded to reflect anti-corrosion measures associated with a corrosion level of the environment onto the design and maintenance of those apparatuses Meanwhile, according to the ISO11844-1 standard, a method for evaluating a corrosion level of copper, silver, aluminum, iron and zinc which are exposed for a predetermined period under an corrosive environment is generally utilized, as a tool for evaluating corrosiveness of the environment installed with electric and electronic apparatuses. It has been well known that copper, silver, aluminum, iron and zinc corrode by such corrosive gases as $SO_2$, $NO_2$, $H_2S$, although a corroded degree of each metal is different each other.

However, the method for evaluating environment and the device using the method in the above conventional technique have the following problems. That is, if an evaluation target is the environment with "a middle level of corrosiveness" in which a failure in electric and electronic apparatuses may occur due to the corrosiveness degree described in the ISO11844-1 standard and a silver film with a thichness of 0.1 μm. (i.e., 100 nm) is used for measuring the time course of the electric resistance value., a detection sensor using such a silver film is merely applicable to the measurement only for about one month. Herein, according to the ISO11844-1 standard, the above middle level of corrosiveness is the environment where a corrosive rate of the exposed silver falls in the range from 105 to 410 nm/year.

Further, if an evaluation target is the environment with "a high level of corrosiveness or "an extremely high level of corrosiveness", a measurable period of the detection sensor becomes shorter than one month. Herein, the environment with the "high level of corrosiveness" is the environment where probability of causing corrosion to influence the reliability of the devices is high, and improvement of the environment is essential, more specifically, where a corrosive rate of the exposed silver falls in the range from 410 to 1050 nm/year. The environment with the "extremely high level of corrosiveness" is the environment where a corrosive rate of the exposed silver falls in the range from 1050 to 2620 nm/year. Accordingly, the above type of detection sensor is not suitable for the long term measurement.

In the meantime, if a thickness of the silver film is elongated, a detection sensor using the elongated film may have a long measurable period. However, this procedure has a drawback that uniformness of the thickness of the film becomes larger as the thickness thereof becomes thicker, which results in deterioration of the measuring accuracy.

Moreover, the method for evaluating environment and the device using the method in the above conventional technique have additional problems. That is, if local corrosion occurs in the sensor unit, more specifically, if dust or salts adheres to the sensor unit and corrosion occurs in the vicinity of the adhering portion, the corrosion makes a measurable period of the sensor unit turn to shorter than the original period essentially provided for the sensor unit.

Furthermore, if a sensor unit (i.e., gas detection element) is directly exposed to the target environment, a corrosive rate varies depending on a flow rate of the corrosive gas present in the target environment, leading to another problem.

SUMMARY OF THE INVENTION

For solving the above problems, an object of the present invention is to provide a device and method for monitoring corrosive environment. The device for monitoring corrosive environment includes at least one passage structure for controlling intrusion of a corrosive substance present in an atmosphere into each passage structure, and a metal film disposed inside each passage structure. Herein, a corroded region of the metal film expands as the corrosive substance intrudes into the device from an opening of the passage structure. The expansion of the corroded region of the metal film changes an electric resistance value of the metal film. Hence, the method for monitoring corrosive environment includes measuring the electric resistance value changed depending on the expansion of the corroded region of the metal film.

According to the present invention, it is possible to accurately determine a corrosion amount of the metal film which corrodes from the opening of the passage structure. Further, it is also possible to suppress fluctuation of the corrosion amount of the metal film, and occurrence of local corrosion in the sensor unit (e.g., corrosion caused near a portion to which dust and/or salts adhere in the sensor unit), or a thickness of the metal film. Herein, it should be noted that the corrosion amount varies depending on a flow rate of a corrosive substance present in the target environment.

Eventually, the above feature of the present invention allows a corrosion level of the environment to be quantified in a more accurate manner.

BRIEF DESCRIPTION OF THE DRAWINGS

FIG. 1 is a top view of a device for monitoring corrosive environment in an embodiment of the present invention.

FIG. 2 is a side view of the device for monitoring corrosive environment in FIG.

FIG. 3 is a front view of the device for monitoring corrosive environment in FIG. 1.

FIG. 4 shows a corrosion state of a metal film measured at Time A after exposing the device for monitoring corrosive environment of FIG. 1.

FIG. 5 shows electric resistance of the metal film measured at Time A after exposing the device for monitoring corrosive environment in FIG. 4.

FIG. 6 shows a front view of the device for monitoring corrosive environment in FIG. 4.

FIG. 7 shows a corrosion state of the metal film measured at Time B after exposing the device for monitoring corrosive environment of FIG. 1 under the corrosive environment.

FIG. 8 shows electric resistance of the metal film measured at Time B after exposing the device for monitoring corrosive environment of FIG. 1 under the corrosive environment.

FIG. 9 shows a front view of the device for monitoring corrosive environment in FIG. 7.

FIG. 42 is a top view of a device for monitoring corrosive environment in still another embodiment of the present invention.

FIG. 43 is a side view of the device for monitoring corrosive environment in FIG. 42.

FIG. 44 is a top view showing an initial state of two metal films respectively made of chromium and silver in the device for monitoring corrosive environment of FIG. 42.

FIG. 45 is a top view showing a corrosion state of the two metal films respectively made of chromium and silver in the sensor unit of the device for monitoring corrosive environment of FIG. 42 after exposing the two films under the corrosive environment.

FIG. 46 is a top view of the sensor unit of FIG. 42.

FIG. 47 is a top view of the sensor unit of FIG. 42.

FIG. 48 is a diagram showing electric resistance of the metal films of FIG. 44.

FIG. 49 is a diagram showing electric resistance of the metal films of FIG. 45.

FIG. 50 shows resistivities and temperature coefficients of resistance (TCR) of the metal films.

DETAILED DESCRIPTION OF THE PRESENT INVENTION

Figure 10:
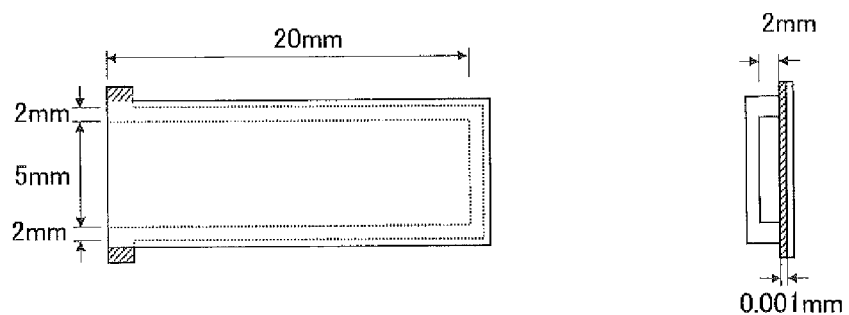
FIG. 10 shows dimensions of the device for monitoring corrosive environment in the present embodiment.

Hereinafter, embodiments for carrying out the present invention will be described in detail referring to the attached drawings.

Next, a device for monitoring corrosive environment which measures a level of corrosion generated by a corrosive substance present in the environment where an electric and electronic apparatus is installed will be described. Further, a method for monitoring corrosive environment will be also described.

FIGS. 1 to 3 are schematic diagrams showing a device for monitoring corrosive environment in an embodiment of the present invention. FIG. 1 is a top view of the device, FIG. 2 is a side view thereof, and FIG. 3 is a front view thereof.

The device for monitoring corrosive environment 1 includes a sensor unit having a metal film 2 that is disposed on an insulating substrate 3 and placed inside a passage structure 4. The sensor unit is fixed as a part of a side wall of the passage structure 4 having an opening 5. The metal film 2 includes a metal film portion 2a exposed inside the passage structure 4 (hereinafter also referred to as exposed portion), and a metal film portion 2b which is extended outside the passage structure 4 to be unexposed inside the passage structure 4 (hereinafter also referred to as unexposed portion). Further, a pair of terminals 8 for measuring an electric resistance value are disposed at the respective ends of the metal film 2. A material of the metal film portions is a metallic material of which electric resistance is different from that of a corroded product of the intact metal such as copper and silver used for corrosion monitoring in the environment installed with an electronic apparatus as well as aluminum, iron, and zinc or the like.

When the device for monitoring corrosive environment 1 is inserted in the target environment, a corrosive substance intrudes into a passage structure 4 from an opening 5 thereof, thereby to corrode the metal film 2. The passage structure 4 has a function to control a corrosive rate of the metal film 2 which is a sensing element for the corrosive substance present in the target environment. More specifically, the passage structure 4 has one opening 5 placed at the left side of the passage structure 4 in FIG. 1. The right side of the passage structure 4 has no opening and is shielded from the surrounding environment. Thus, a flow 6 of the corrosive substance in the surrounding atmosphere can not intrude into the inside of the passage structure 4 through the opening 5, even though the corrosive substance approaches the opening 5.

On the contrary, in a conventional device for monitoring corrosive environment, a metal film directly contacts with a flow of the surrounding atmosphere. Therefore, a corrosion quantity of the metal film becomes larger as the flow of the surrounding atmosphere becomes faster in the prior art. However, according to the present invention, a corrosive substance located in the vicinity of the opening 5 of the passage structure 4 may intrude through the opening 5 in the diffusing direction 7 of the corrosive substance (i.e., arrow 7 in FIG. 3). In other words, only the diffusion phenomenon allows the corrosive substance to intrude inside the passage structure 4. Accordingly, the device for monitoring corrosive environment 1 of the present invention is capable of measuring a corrosion level of the corrosive substance without being influenced by the flow of the surrounding atmosphere.

As mentioned above, in the present invention, the direction to which the metal film corrodes is fixed, allowing fluctuation of the measured values to be decreased. Here, it should be noted that the corrosive substance includes a corrosive gas, flying sea salt and dust or the like but hereinafter a corrosive gas represents the corrosive substance in the following descriptions.

Next, a method for quantifying a corrosive gas diffused inside the passage structure 4 to be located in the vicinity of the opening 5 will be described in detail.

As shown in FIG. 1, a diffusing direction of the corrosive gas is restricted in the way from the left to right side of paper in the drawing so as to control corrosion of the sensor unit of the device for monitoring corrosive environment 1. Since the flux density of the corrosive gas becomes larger as the distance between the gas and the opening 5 becomes shorter, a corrosion quantity of the metal film 2 becomes larger as the location becomes closer to the left side of the film 2. This phenomenon is described in a reference: Zairyo To Kankyo (Material and Environment), vol. 56, pp. 265-271 (2007), "Assumption of Corrosive Rate of Silver in Sulfur Gas Environment". In the reference, the authors observe that a corrosive rate of a metallic plate becomes smaller as the distance of the metallic plate from the generation source of the corrosive gas becomes longer via conducting experiments using metallic plates and analysis of the experimental results. The above procedure allows analysis on the corrosion phenomenon of the device for monitoring corrosive environment.

Next, FIGS. 4 to 9 respectively show a corroded status of the metal film after the device for monitoring corrosive environment has been exposed in the corrosive environment. As shown in FIGS. 4 and 5, the region already corroded with a corrosion thickness equal to the thickness of the metal film not corroded. Herein, the above region means an area where the metal film has been corroded downward to the interface between the substrate and the metal film. The corrosive gas 6 present in the environment continuously diffuses from the left side of the metal film proximal to the opening 5, thereby to corrode the metal film toward the right side thereof. As shown in FIGS. 4 and 7, the region 9 where the metal film has been entirely corroded in the thickness direction more expands at Time B (i.e., length Lb) than at Time A (i.e., length La). In the metal film portion 2a exposed inside the passage structure 4, the region 9 which has been entirely corroded in the thickness direction is formed, while the metal film portion 2b unexposed inside the passage structure 4 remains intact. As a result, a region where a cross-sectional area of the metal film 2 locally decreases between the terminals 8 is formed (see FIG. 6).

As shown in FIGS. 5 and 8, the electric resistance value between the terminals 8 is represented as 2Ra+Rm at Time A, and 2Rb+Rm. at Time B. This is calculated by adding the electric resistance value Ra of the region where the cross-sectional area of the metal film 2 locally decreases to the electric resistance value Rm of the metal film 2. Herein, since there are relationships that Rm<<Ra, and Rm<<Rb, Rm at Time A is assumed to be equal to Rm. at Time B. Further, as shown in FIGS. 6 and 9, in the metal film 2, a surface side of the metal film 2 inside the passage structure 4 is partially corroded in addition to the region 9 of the metal film 2 entirely corroded. However, to make the description simpler, the partial corrosion of the surface side of the metal film 2 will not be taken into consideration, hereinafter.

Figure 11:
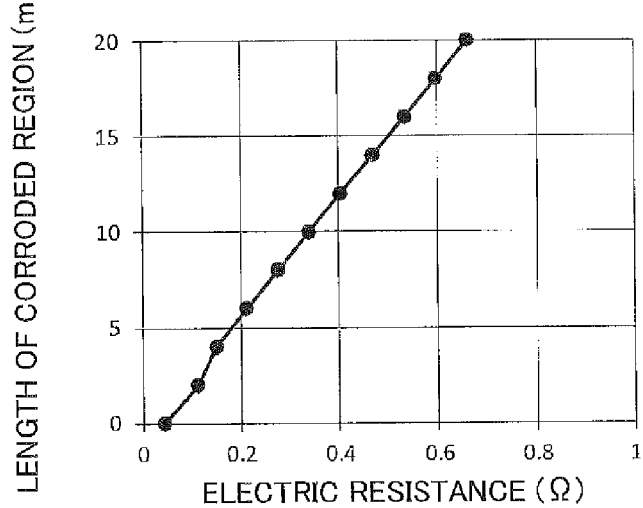
FIG. 11 shows a relationship between the electric resistance which is an output of the device for monitoring corrosive environment (i.e., sensor unit) and a length of the corroded region 9 where the entire film in the thickness direction has been corroded in the metal film of the device for monitoring corrosive environment (i.e. sensor unit).
Figure 12:
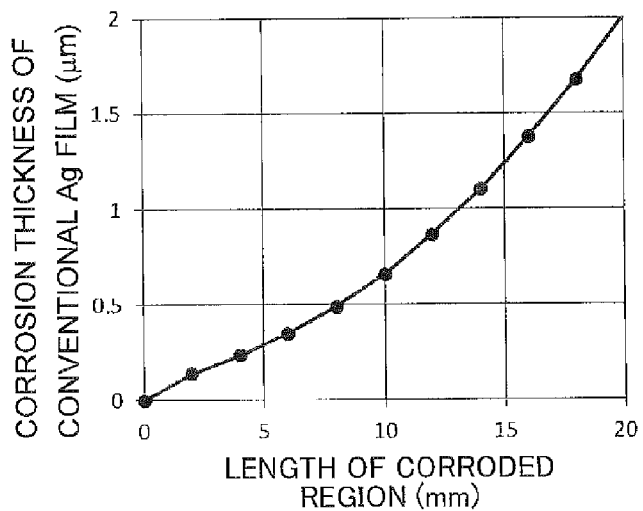
FIG. 12 shows a relationship between a length of the corroded region 9 where the entire film in the thickness direction has been corroded in the metal film of the device for monitoring corrosive environment (i.e., sensor unit) and a corrosion thickness of the conventional metal film (i.e., silver film).

Next, analytical results of the device for monitoring corrosive environment having such dimensions as shown in FIG. 10 will be described. Here, as the metal film of a sensor unit, a silver film of 100 nm with specific resistance of 1.59E-5 Ωm is used. FIG. 11 shows a relationship between an electric resistance value (i.e., output) of the device for monitoring corrosive environment of the present embodiment and a corrosion length of the region 9 where the entire metal film has been corroded in the thickness direction in the device for monitoring corrosive environment. Further, FIG. 12 shows a relationship between a corrosion length of a region 9 where the entire metal film is corroded in the thickness direction thereof and a corrosion thickness of the metal film (i.e., silver film) used in the conventional process.

As mentioned above, the device for monitoring corrosive environment is exposed in the target environment. Then, the electric resistance value of the sensor unit is measured, and a corrosion thickness of the metal film is calculated based on the measured value. Associated with the corrosion thickness, a corrosion level of the surrounding atmosphere is classified complying with the IEC654-4 standard, ISO11811-4 standard, ISO9223 standard, and ISA71.04. Note that the region 9 of the metal film, where the entire film has been corroded in the thickness direction, may be visually observed by applying a transparent substrate to the insulating substrate 3. This arrangement allows a life-time of the sensor unit to be determined on the spot. In short, the higher the concentration of the corrosive gas in the evaluating environment becomes, the more the corrosive rate of the metal film increases, and the more the electric resistance value of the sensor unit increases.

Figure 13:
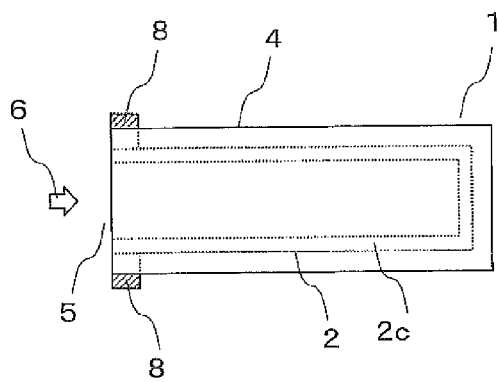
FIG. 13 is a top view of a device for monitoring corrosive environment in another embodiment of the present invention.
Figure 14:
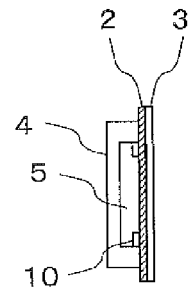
FIG. 14 is a side view of the device for monitoring corrosive environment in FIG. 13.

FIGS. 13 and 14 are schematic diagrams showing another embodiment of the device for monitoring environment device. FIG. 13 is a top view of the device and FIG. 14 is a side view thereof. The device for monitoring environment device 1 is provided with a sensor unit including a metal film 2 disposed on an insulating substrate 3. The sensor unit is fixed as a part of a side wall of a passage structure 4 having an opening 5. The metal film 2 includes a metal film portion 2a exposed inside the passage structure 4 and a metal film portion 2c (hereinafter referred to as uncoated portion) covered by a coating 10 to be unexposed inside the passage structure 4. At both ends of the metal film 2, a pair of terminals 8 are respectively disposed to measure the electric resistance value.

Figure 15:
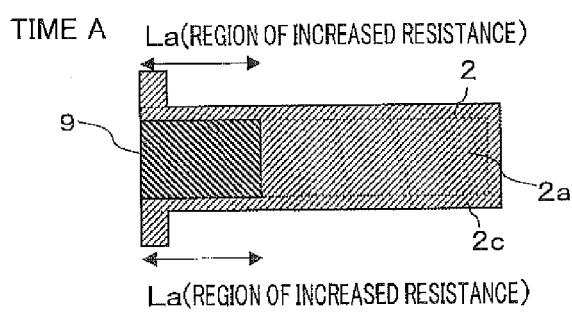
FIG. 15 shows a corrosion state of a metal film measured at Time A after exposing the device for monitoring corrosive environment of FIG. 13 under the corrosive environment.
Figure 17:
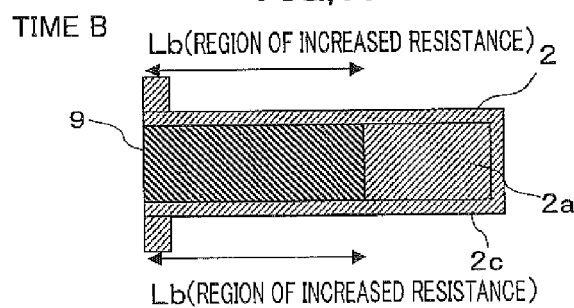
FIG. 17 shows a corrosion state of the metal film measured at Time B after exposing the device for monitoring corrosive environment of FIG. 13 under the corrosive environment.
Figure 18:
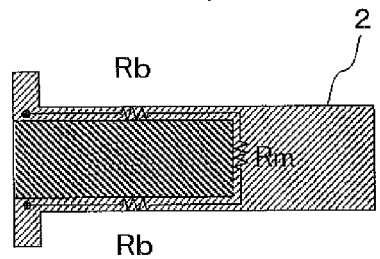
FIG. 18 shows electric resistance of the metal film measured at Time B after exposing the device for monitoring corrosive environment of FIG. 13 under the corrosive environment.

A corrosive gas 6 present in the corrosive environment is continuously diffusing from the left side near the opening 5, and further corrodes the right side of the metal film 2. As shown in FIGS. 15 and 17, a region 9 of the metal film 2, where the entire film has been corroded in the thickness direction, more expands to the right side thereof at Time B (i.e., length Lb) than at Time A (length La). Accordingly; the region 9 is formed in the metal film portion 2a, via being exposed inside the passage structure 4 to be corroded in the entire thickness direction thereof, and the metal film portion 2c remains intact which is covered by a coating 10 and unexposed inside the passage structure 4.

Figure 16:
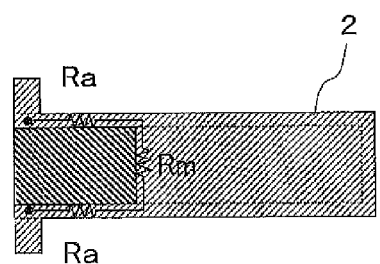
FIG. 16 shows electric resistance of the metal film measured at Time A after exposing the device for monitoring corrosive environment of FIG. 13 under the corrosive environment.

As shown in FIGS. 16 and. 18, the electric resistance value between the pair of terminals 8 is represented as 2Ra+Rm at Time A and 2Rb+Rm at Time B respectively, by adding the electric resistance value Ha or Rb in the region where the cross-sectional area of the metal film locally decreases, to the electric resistance value Rm of the metal film 2. This configuration enables the metal film portion 2c unexposed by the coating 10 to exert the same effect as in the metal film portion 2b unexposed inside the passage structure 4 of the embodiment in FIG. 1.

Figure 19:
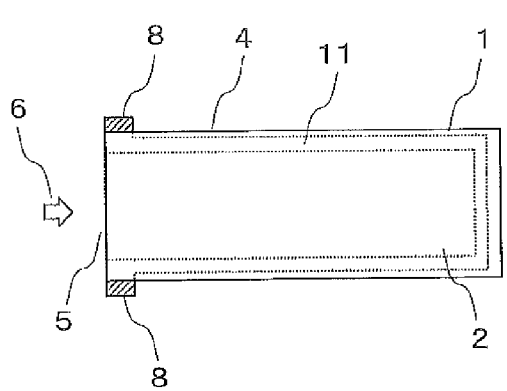
FIG. 19 is a top view of a device for monitoring corrosive environment in another embodiment of the present invention.
Figure 20:
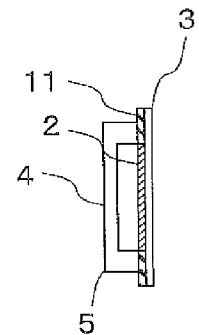
FIG. 20 is a side view of the device for monitoring corrosive environment of FIG. 19.

FIGS. 19 and 20 are schematic diagrams showing still another embodiment of the device for monitoring corrosive environment 1. FIG. 19 is a top view of the device and FIG. 20 is a side view thereof. The device for monitoring corrosive environment 1 is provided with a sensor unit including a metal film disposed on an insulating substrate 3, and fixed as a part of a side wall of a passage structure 4 having an opening 5. The metal film includes a first metal film 2 exposed inside the passage structure 4, and a second metal film 11 arranged at the periphery of the first metal film 2 exposed inside the passage structure 4. The second metal film 11 is made of a material which never corrodes in the target environment including, for example, titanium, chromium, gold, palladium, and silver-palladium alloy.

Figure 21:
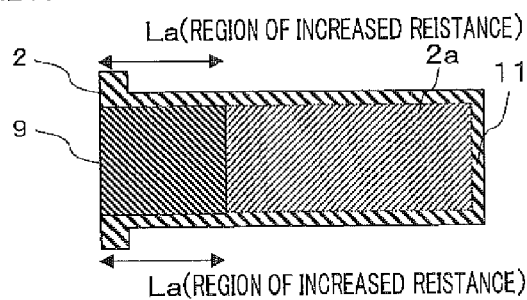
FIG. 21 shows a corrosion state of the metal film measured at Time A after exposing the device for monitoring corrosive environment of FIG. 19 under the corrosive environment.
Figure 22:
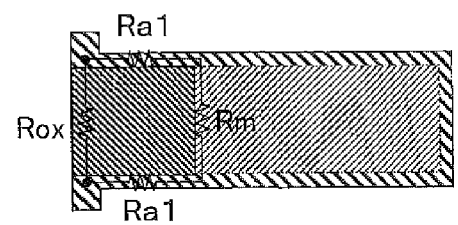
FIG. 22 shows electric resistance of the metal film measured at Time A after exposing the device for monitoring corrosive environment of FIG. 19 under the corrosive environment.
Figure 23:
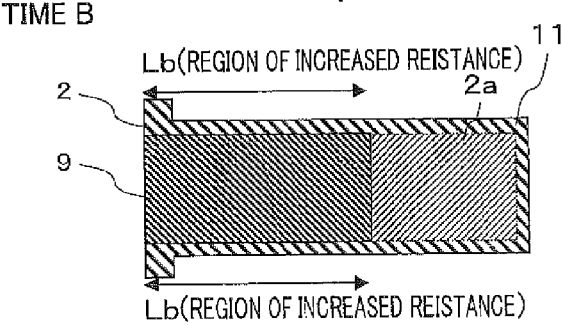
FIG. 23 shows a corrosion state of the metal film measured at Time B after exposing the device for monitoring corrosive environment of FIG. 19 under the corrosive environment.
Figure 24:
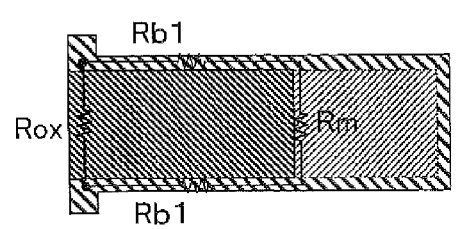
FIG. 24 shows electric resistance of the metal film measured at Time B after exposing the device for monitoring corrosive environment of FIG. 19 under the corrosive environment.

As shown in FIGS. 21 and 23, the region 9 of the metal film, which is corroded. In the entire thickness direction of the metal film, more expands to the right side at Time B (i.e., length Lb) than at Time A (length La). That is, the region 9 is formed, which is a part of the metal film 2 to be corroded in the entire thickness thereof exposed inside the passage structure 4, while only the second metal film 11 not corroding in the target environment remains intact alone among the conduction portions. As shown in FIGS. 22 and 24, the electric resistance value between the pair of terminals 8 is represented as 2Ra1+Rm at Time A and 2Rb1+Rm at Time B respectively, by adding the electric resistance value Ra1 or Rb1 of the second metal film 11 in the region where only the second metal film 11 not corroding in the target environment remains intact alone, to the electric resistance value Rm of the first metal film 2.

Herein, the electric resistance value Rox of the region 9 corroded in the entire thichness direction thereof decreases time-dependently as the region expands. However, the influence of the electric resistance value Rox is negligible due to the relationship of Ra1<Rox at the initial stage. The second metal film 11 not corroding in the target environment is provided in order to exert the same effect as of the metal film portion 2b unexposed inside the passage structure 4 in FIG. 1 and the metal film portion 2c unexposed inside the passage structure 4 by the coating 10 in FIG. 14.

In the device for measuring corrosive environment of the present embodiment, measured is the resistance of the sensor unit, more specifically, the electric resistance value of the second metal film 11 in the region where only the second metal film 11 not corroding in the target environment remains intact. Therefore, if a metallic material with large specific resistance is selected for the second metal film 11 of the sensor unit, it is possible to increase the sensitivity of the sensor unit. For example, the specific resistance value of titanium (i.e., 4.27E·7 Ωm) is 25 times larger than that of silver i.e., 1.59E·8 Ωm) which is used as the metal film of the sensor unit. Further, the sensitivity of the sensor unit becomes 250 times higher by making the thickness of the titanium film 10 times thinner than that of the silver film (here, 1 μm).

Figure 36:
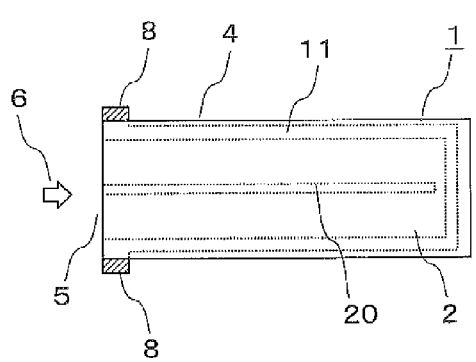
FIG. 36 is a top view of a device for monitoring corrosive environment in still another embodiment of the present invention.
Figure 37:
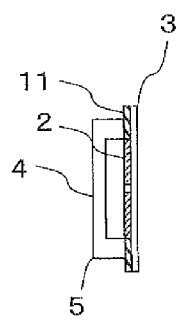
FIG. 37 is a side view of the device for monitoring corrosive environment in FIG. 36.
Figure 38:
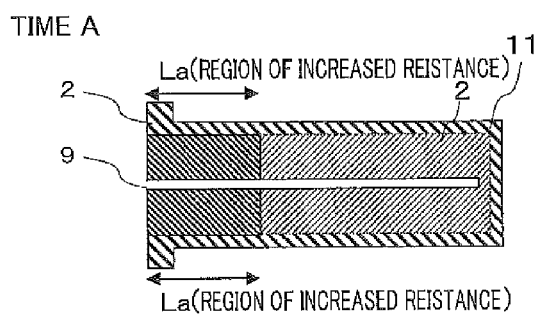
FIG. 38 is a top view showing a corrosion state of the metal film measured at Time A after exposing the device for monitoring corrosive environment of FIG. 36 under corrosive environment.
Figure 39:
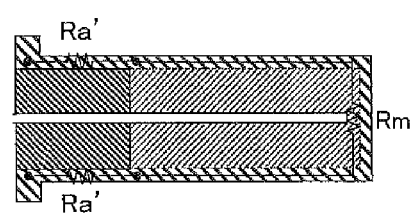
FIG. 39 shows electric resistance of the metal film measured at Time A after exposing the device for monitoring corrosive environment of FIG. 25 under the corrosive environment.
Figure 40:
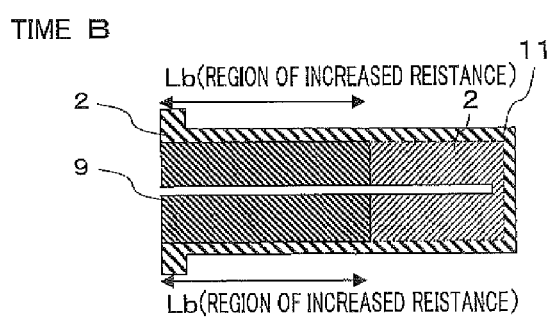
FIG. 40 is a top view showing a corrosion state of the metal film measured at Time B after exposing the device for monitoring corrosive environment of FIG. 36 under corrosive environment.
Figure 41:
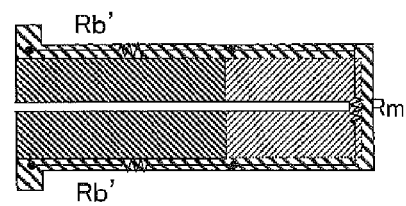
FIG. 41 shows electric resistance of the metal film measured at Time B after exposing the device for monitoring corrosive environment of FIG. 36 under the corrosive environment.

Meanwhile, if the electric resistance value Rox decreases to fulfill a relationship of Ra1>Rox as the region 9 corroded in the entire thickness direction of the metal film more expands, the electric resistance value between the pair of terminals 8 does not become proportional to the expansion of the region 9 thus corroded. Accordingly, when the configuration of the device in the present embodiment is applied, it is necessary to take care of the relationship between the electric resistance value Ra1 and the electric resistance value Rox, Next, FIGS. 36 and 37 are schematic diagrams showing still another embodiment of the device for monitoring corrosive environment. A feature of the device in this embodiment is that a slit 20 is formed in the first metal film 2 in the device of FIGS. 19 and 20, in a longitudinal direction of the first metal film 2 to which a corrosive gas diffuses. As shown in FIGS. 38 to 41, this configuration allows the relationship of Rox>Rm to be always kept. As a result, although the electric resistance value Rox decreases time-dependently as the region 9 mote expands, the relationship of Ra1<Rox is kept the same as in the initial stage. Thus, the electric resistance value between the pair of terminals 8 is proportional to the expansion of the region 9 thus corroded.

Figure 25:
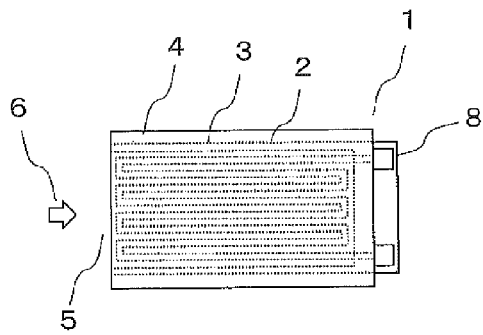
FIG. 25 is a top view of a device for monitoring corrosive environment in still another embodiment of the present invention.
Figure 26:
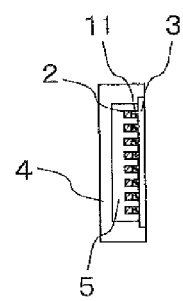
FIG. 26 is a side view of the device for monitoring corrosive environment in FIG. 25.
Figure 27:
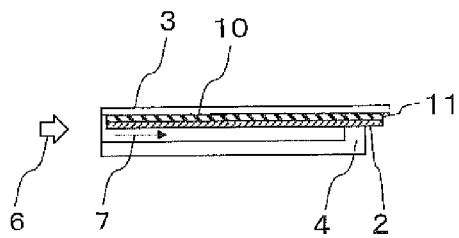
FIG. 27 is a front, view of the device for monitoring corrosive environment in FIG. 25.

FIGS. 25 to 27 are schematic diagrams showing still another embodiment of the device for monitoring corrosive environment. FIG. 25 is a top view of the device, FIG. 26 is a side view thereof, and FIG. 27 is a front view thereof. The device for monitoring corrosive environment 1 is provided with a sensor unit including two-layered metal film disposed on an insulating substrate 3. The sensor unit is fixed as a part of a side wall of a passage structure 4 having an opening 5. The metal film include a first metal film 2 exposed inside a passage structure 4, and a second metal film 11 disposed on the undersurface of the first metal film 2 exposed inside the passage structure 4. The second metal film 11 is made of a metallic material not corroding in the target environment, including, for example, titanium, chromium, gold, palladium, silver-palladium alloy. Herein, even when the first metal film 2 and the second metal film 11 are formed as zigzag electrodes, the device for monitoring corrosive environment in the present embodiment exerts the same effect as of the devices shown in FIGS. 1, 13 and 19.

Figure 28:
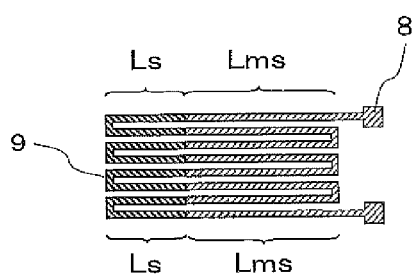
FIG. 28 shows a corrosion state of the metal film measured at Time A after exposing the device for monitoring corrosive environment of FIG. 25 under corrosive environment.
Figure 29:
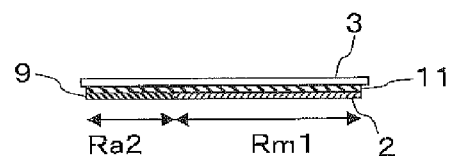
FIG. 29 shows electric resistance of the metal film measured at Time A after exposing the device for monitoring corrosive environment of FIG. 25 under the corrosive environment.
Figure 30:
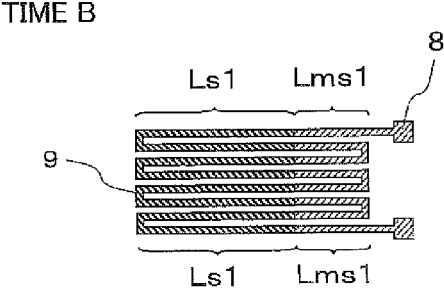
FIG. 30 shows a corrosion state of the metal film measured at Time B after exposing the device for monitoring corrosive environment of FIG. 25 under the corrosive environment.
Figure 31:
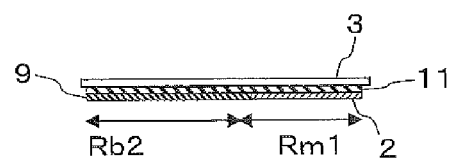
FIG. 31 shows electric resistance of the metal film measured at Time B after exposing the device for monitoring corrosive environment of FIG. 25 under the corrosive environment.

As shown in FIGS. 28 and 30, the region 9 which is corroded in the entire thickness direction of the first metal film 2 more expands to the right side at Time B (length Ls1) than at Time A (length Ls). Since the region 9 of the first metal film 2 exposed inside the passage structure 4 is corroded. In the entire thickness direction of the film, only the second metal film 11 not corroding in the target environment remains alone intact among the conduction portions. As shown in FIGS. 29 and 31, the electric resistance value of one line of the zigzag electrodes including the first metal film 2 and the second metal film 11 is represented as Ra2+Rm1 at Time A and Rb2+Rm1 at Time B respectively; by adding the resistance value Ra2 or Rb2 of the second metal film 11 in the region where only the second metal film 11 not corroding in the target environment remains alone intact, to the electric resistance value Rm1 of the first metal film 2. Since the zigzag electrodes are formed of a plurality of lines arranged in series, the electric resistance value between the pair of terminals 8 is equal to a value calculated via multiplying the electric resistance value per one line as mentioned above by the number of the total lines arranged in the zigzag electrodes.

Figure 32:
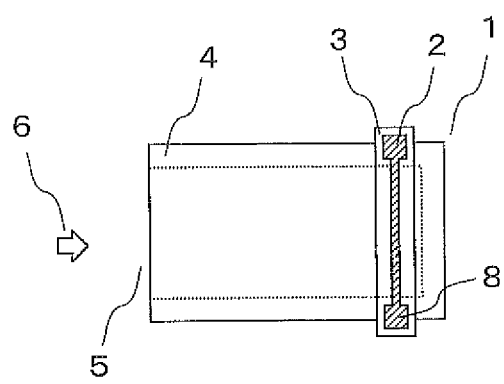
FIG. 32 is a top view of a device for monitoring corrosive environment in still another embodiment of the present invention.
Figure 33:
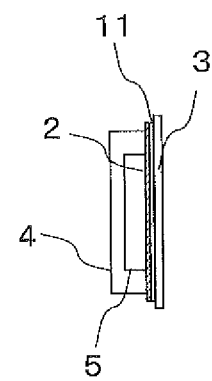
FIG. 33 is a side view of the device for monitoring corrosive environment in FIG. 32.

Meanwhile, in the device for monitoring corrosive environment shown in FIG. 19, the sensitivity of the sensor unit is improved by using the second metal film 11 having large specific resistance and a thin film thickness. In the present embodiment of FIG. 25, it is possible to further improve the measurement sensitivity of the sensor unit by elongating the total length of the electrodes via applying zigzag electrodes to the sensor unit, in addition to by using the second metal film 11 having large specific resistance and a thin film thickness. Note that the zigzag electrode may be formed as only one line as shown in FIGS. 32 and 33.

Next, FIGS. 42 and 43 are schematic diagrams showing still another embodiment of the device for monitoring corrosive environment. FIG. 42 is a top view of the device and FIG. 43 is a side view thereof. The device for monitoring corrosive environment 1 is provided with a sensor unit including two metal films disposed on an insulation substrate 3. The sensor unit is fixed as a part of a side wall of a passage structure 4 having an opening 5. The metal films include a first metal film 2 exposed inside a passage structure 4, and a second metal film 11 disposed on the undersurface of the first metal film 2 exposed inside the passage structure 4. The second metal film 11 is made of a metallic material not corroding in the target environment, including, for example, titanium, chromium, gold, palladium, silver-palladium alloy. Herein, the feature of the sensor unit is that the first metal film 2 has a broader width than the second metal film 11.

As shown in FIG. 50, the measured resistivity of the first metal film 2 (i.e., silver film) is 20 times smaller than that of the second metal film 11 (i.e., chromium film). On the contrary, the temperature coefficient of resistance (TCR) of the silver film is 100 times larger than that of the chromium film. As shown in FIGS. 48 and 49, the electric resistance value between the pair of terminals 8 depends on the electric resistance value of the silver film at the initial stage of the monitoring period and does not depend on the electric resistance value of the chromium film. As the corrosion proceeds, in the region 9 where the silver film is corroded (i.e., changed to $Ag_2S$) in the entire thickness direction of the silver film, the electric resistance value between the pair of terminals 8 depends on the electric resistance value of the chromium film located in the corroded region 9. Further, in the region where the silver film is not corroded, the electric resistance value between the pair of terminals 8 depends on the electric resistance value of the silver film located in the non-corroded (i.e., intact) region.

In the meantime, the device for monitoring corrosive environment in the present invention may be set in the environment where a temperature therein fluctuates. Herein, a material having a small temperature coefficient of resistance (TCR) is preferable for configuring a sensor unit. As described above, the TCR of the chromium film is small, while the TCR of the silver film is 100 times larger than that of the chromium film. Therefore, in the present embodiment, preferably the device for monitoring corrosive environment may have a sensor unit configured to minimize the fluctuation of the electric resistance value of the silver film.

As shown in FIG. 44, in the present invention, a width of the silver film (i.e., $W_{Ag}$) is made longer than that of the chromium film (i.e., War). If the electric resistance value of the silver film becomes smaller, the fluctuation of the electric resistance value between the pair of terminals 8 becomes smaller. Further, the devices in FIGS. 1, 13, and 19 have the same effect as in the present embodiment. Herein, when a transparent insulating substrate 3 is used, it is possible to assume a corrosion level of the environment based on a length of the corroded region which is checked through the substrate side. Moreover, the first metal film 2 and the second metal film 11 may be formed, as zigzag electrodes, for example, in the case of FIGS. 36 and 37.

Figure 34:
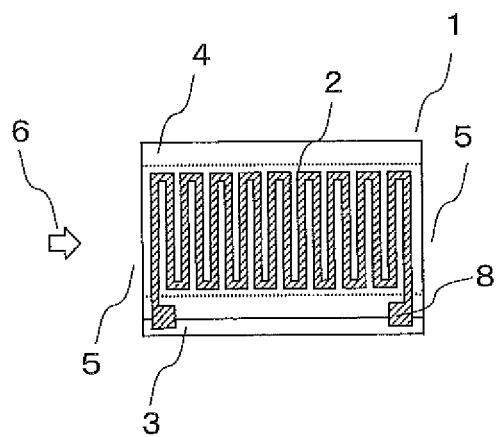
FIG. 34 is a top view of a device for monitoring corrosive environment in still another embodiment of the present invention.
Figure 35:
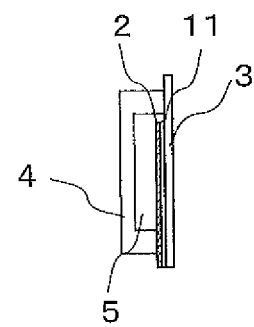
FIG. 35 is a side view of the device for monitoring corrosive environment in FIG. 34.

Next, FIGS. 34 and 35 are schematic diagrams showing still another embodiment of the device for monitoring corrosive environment. FIG. 34 is a top view of the device and FIG. 35 is a side view thereof. The device for monitoring corrosive environment 1 is provided with a sensor unit including a two-layered metal film disposed on an insulation substrate 3. The sensor unit is fixed as a part of a side wall of a passage structure 4 having two openings 5 respectively at the left and right sides of the passage structure 4. The two-layered metal film is composed of a first metal film 2 exposed inside the passage structure 4, and a second metal film 11 disposed on the undersurface of the first metal film 2 exposed inside the passage structure 4. The second metal film 11 is made of a metallic material not corroding in the target environment, including, for example, titanium, chromium, gold, palladium, silver-palladium alloy. As mentioned above, the arrangement of the openings 5 at the left and right sides of the passage structure 4 enables the influence of an air flow in the surrounding corrosive environment caused by a corrosive gas to be evaluated.

The device for monitoring corrosive environment of the present invention may independently have a measurement system. Further, the device for monitoring corrosive environment may be configured to use a measurement system formed on a printed circuit board in advance via mounting the measurement system thereon. Mounting of the measurement system on the printed circuit board allows the electronic apparatus to perform self-diagnosis.

Hereinbefore, the device for monitoring corrosive environment including a sensor unit provided with a metal film has been described in the previous embodiments. That is, in those embodiments, a corrosive gas present in the target environment intrudes from the outside into a gas introduction passage (i.e., passage structure) and successively corrodes the metal film from an opening side of the device. A corroded region of the metal film generated by the corrosive gas successively expands time-dependently. Under this condition, the device for monitoring corrosive environment measures the electric resistance value of the metal film, in which the electric resistance value increases corresponding to the increase in the corroded region of the metal film. Measurement of the electric resistance value of the sensor unit quantitatively determines a corrosion level of the target environment.

Here, note that the method, in which a metal film successively corrodes from an opening side generated by a corrosive gas intruding from the outside into a gas introduction passage, may be applicable to a quartz oscillator microbalance analysis. Further, in order to suppress the fluctuation of the electric resistance value between the pair of terminals 8 caused by temperature fluctuation, it is effective to arrange a temperature compensating sensor unit in the device for monitoring corrosive environment.

In the present invention, the device for monitoring corrosive environment is not needed to include a large sized structure such as a gas introduction unit using a suction pump, which performs measurement in the environment with a constant flow rate. Thus, the device for monitoring corrosive environment of the present invention is configured to consume less electricity and easily monitor the corrosive environment. Further, the device for monitoring corrosive environment of the present invention is configured to include the opening in a part of the passage structure, and the metal film covered by the passage structure. Thus, this configuration allows the device for monitoring corrosive environment to accurately determine the corroded quantity of the metal film thus corroded from the opening, and suppress the local corrosion of the sensor unit or suppress the fluctuation of the corroded quantity that varies depending on the thickness of the metal film. Herein, the local corrosion of the sensor unit described above means the corrosion caused by dust and salts in the vicinity of the portion to which the dust and salts are attached.

What is claimed is:

1. A device for monitoring corrosive environment comprising:
   a sensor unit;
   at least one passage structure each of which is formed together with the sensor unit so as to control intrusion of a corrosive substance present in an atmosphere; and
   a metal film included in the sensor unit and disposed inside the at least one passage structure, wherein
   an electric resistance value of the metal film varies depending on expansion of a corroded region of the metal film generated by the corrosive substance intruding from an opening of the passage structure;
   the device for monitoring corrosive environment is configured to measure the electric resistance value of the metal film,
   the metal film includes an exposed portion that is exposed to the atmosphere, the exposed portion having a rectangular shape, and
   the metal film also includes an unexposed portion that is unexposed to the atmosphere, the unexposed portion being disposed around an outer perimeter of the rectangular shape and being in direct contact with at least three different sides of the rectangular shape.

2. The device for monitoring corrosive environment according to claim 1, wherein
   the passage structure includes the single opening and the metal film disposed on an insulating substrate and placed inside the passage structure and;
   the corroded region of the metal film expands in a diffusing direction of the corrosive substance intruding from the opening into the passage structure; and the device for monitoring corrosive environment is configured to measure the electric resistance value which increases depending on the expansion of the corroded region.

3. The device for monitoring corrosive environment according to claim 1, wherein
the unexposed portion electrically is connected to the exposed portion; and
the device for monitoring corrosive environment is configured to measure a sum of electric resistance values by adding an electric resistance value of the exposed portion and an electric resistance value of the unexposed portion.

4. The device for monitoring corrosive environment according to claim 3, wherein the electric resistance value of the unexposed portion increases depending on the expansion of the corroded region.

5. The device for monitoring corrosive environment according to claim 3, wherein the unexposed portion includes a coated portion formed by coating a part of the metal film so that the coated portion is not exposed in the atmosphere.

6. The device for monitoring corrosive environment according to claim 2, wherein the metal film is comprised of a first metal film which corrodes by the corrosive substance present in the atmosphere and a second metal film which does not corrode by the corrosive substance present in the atmosphere, wherein
the device for monitoring corrosive environment is configured to measure a sum of electric resistance values by adding an electric resistance value of the first metal film and an electric resistance value of the second metal film.

7. The device for monitoring corrosive environment according to claim 6, wherein the electric resistance value of the second metal film increases depending on the expansion of the corroded region.

8. The device for monitoring corrosive environment according to claim 1, wherein
the passage structure includes the at least one opening and the metal film comprised of a first metal film and a second metal film,
the second metal film not corroding by the corrosive substance present in the atmosphere, being formed in a zigzag shape consisting of a single line or a plurality of lines, disposed on an insulating substrate, and placed inside the passage structure, and
the first metal film being superimposedly disposed on the second metal film; and
the device for monitoring corrosive environment is configured to measure electric resistance values of the first and second metal films,
the electric resistance values varying depending on the expansion of the corroded region of the first metal film generated by the corrosive substance intruding from the opening of the passage structure.

9. The device for monitoring corrosive environment according to claim 6, wherein a material of the second metal film is selected from at least one member of titanium, chromium, gold, palladium, and silver-palladium alloy.

10. The device for monitoring corrosive environment according to claim 1, wherein a material of the metal film is selected from at least one member of titanium, chromium, gold, palladium, and silver-palladium alloy.

11. The device for monitoring corrosive environment according to claim 2, wherein a transparent substrate is used for the insulating substrate.

12. A method for monitoring corrosive environment based on a corrosion level of a metal film disposed inside at least one passage structure that is configured to control intrusion of a corrosive substance present in the environment into the at least one passage structure,
the method comprising the steps of:
measuring an electric resistance value of the metal film, wherein the electric resistance value varies depending on expansion of a corroded region of the metal film generated by the corrosive substance intruding from an opening of the passage structure; and
quantifying the corrosion level of the environment based on the electric resistance value thus measured, wherein
the metal film includes an exposed portion that is exposed to the atmosphere, the exposed portion having a rectangular shape, and
the metal film also includes an unexposed portion that is unexposed to the atmosphere, the unexposed portion being disposed around an outer perimeter of the rectangular shape and being in direct contact with at least three different sides of the rectangular shape.

13. The device for monitoring corrosive environment according to claim 6, wherein a slit is formed in the first metal film in a longitudinal direction thereof to which the corrosive substance diffuses.

14. The device for monitoring corrosive environment according to claim 13, wherein the electric resistance value of the second metal film increases depending on the expansion of the corroded region.

15. The device for monitoring corrosive environment according to claim 6, wherein
the sensor unit is fixed as a side wall of the passage structure;
the second metal film is disposed on an undersurface of the first metal film that is exposed inside the passage structure, in the sensor unit; and
the first metal film has a broader width than the second metal film, in the sensor unit.

16. The device for monitoring corrosive environment according to claim 15, wherein a material of the first metal film is silver, and a material of the second metal film is chromium.

17. The device for monitoring corrosive environment according to claim 15, further comprising a temperature compensating sensor unit.

* * * * *